United States Patent [19]

Huttunen

[11] Patent Number: 5,029,593
[45] Date of Patent: Jul. 9, 1991

[54] DEVICE FOR CLEANING OF THE TEETH

[76] Inventor: Paavo Huttunen, Lustokuja 10, SF-70150 Kuopio, Finland

[21] Appl. No.: 443,368

[22] Filed: Nov. 30, 1989

[30] Foreign Application Priority Data

Jun. 1, 1987 [FI] Finland .................. 872426

[51] Int. Cl.$^5$ ............................. A61C 15/00
[52] U.S. Cl. ..................... 132/323; 132/325
[58] Field of Search ............. 132/323, 324, 325, 326, 132/327

[56] References Cited

U.S. PATENT DOCUMENTS

| | | | |
|---|---|---|---|
| 2,187,899 | 1/1940 | Henne | 132/323 |
| 2,443,415 | 6/1948 | Buscarino | 132/91 |
| 2,444,638 | 7/1948 | Dobbins | 132/92 |
| 2,736,327 | 2/1956 | Schlicksupp | 132/91 |
| 2,784,722 | 3/1957 | Chamberlin et al. | 132/92 |
| 3,376,876 | 4/1968 | Wicklund | 132/92 |
| 3,747,612 | 7/1973 | Davis | 132/92 R |
| 3,828,804 | 8/1974 | Ely | 132/323 |
| 3,834,404 | 9/1979 | Chien | 132/323 |
| 3,871,393 | 3/1975 | Wharton | 132/92 A |
| 3,903,907 | 9/1975 | Knaus | 132/92 R |
| 4,427,018 | 1/1984 | Lagace | 132/323 |
| 4,657,033 | 4/1987 | Dalton | 132/91 |

FOREIGN PATENT DOCUMENTS 577198 6/1959 Canada .................. 132/324
2074876 11/1981 United Kingdom .
2183485 6/1987 United Kingdom .

Primary Examiner—Robert P. Swiatek
Assistant Examiner—Nicholas D. Lucchesi
Attorney, Agent, or Firm—Cushman, Darby & Cushman

[57] ABSTRACT

A device for cleaning teeth is disclosed as having a shaft for containing dental floss and floss holders. Wedge shaped fastening grooves in the floss holders hold the dental floss tightly between the floss holders. In operation, the segment of floss held between the floss holders is useable to clean between teeth.

4 Claims, 2 Drawing Sheets

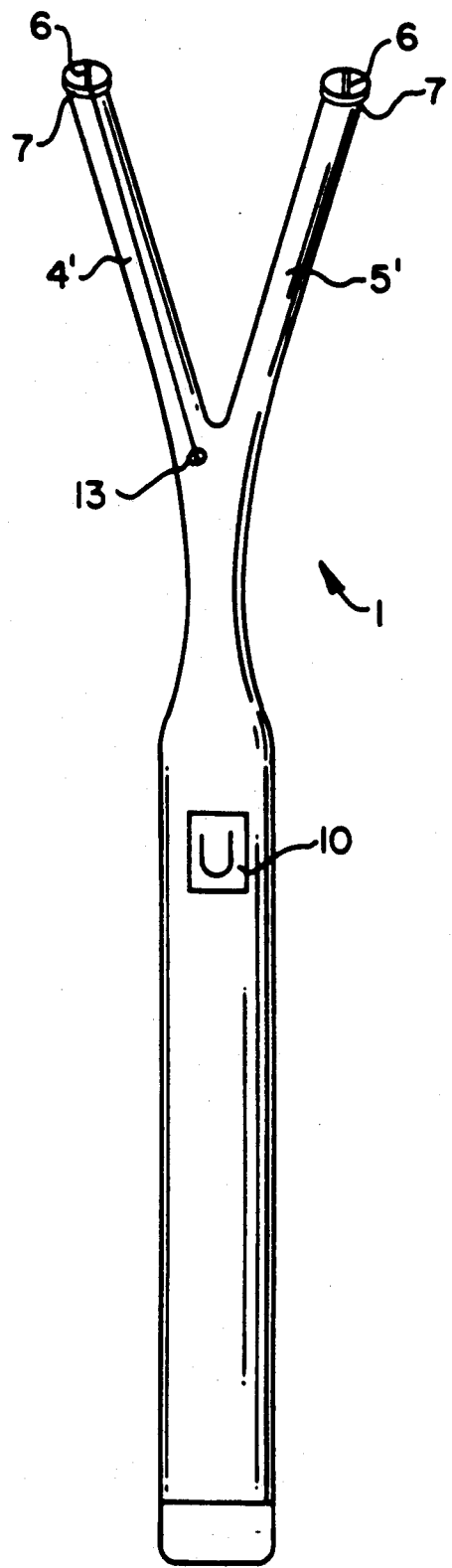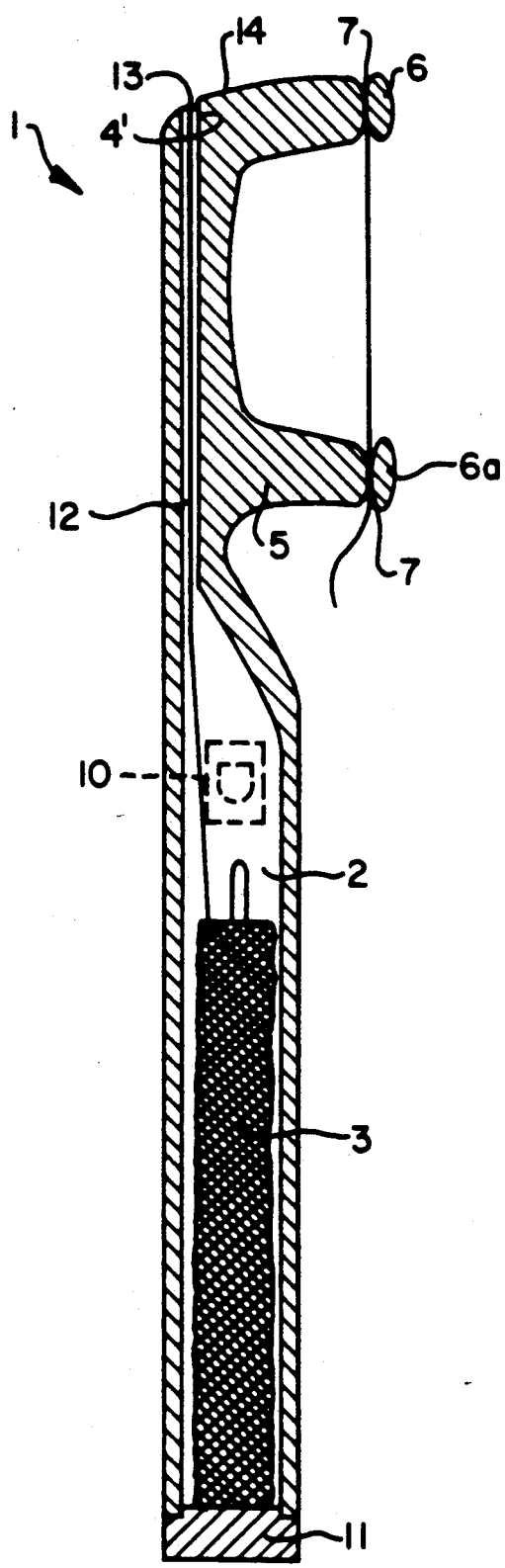

DEVICE FOR CLEANING OF THE TEETH

This is a continuation-in-part of my International Application PCT/FI88/00084 filed May 31, 1988 which designated the United States.

FIELD OF THE INVENTION

The object of the present invention is a device for cleaning teeth. In particular the present invention is a device which has a shaft with dental floss contained therein, and two floss holders with fastening grooves provided to hold the floss in tension between the two floss holders.

BACKGROUND OF THE INVENTION

With the help of the dental floss the interdental spaces can be efficiently cleaned and thus prevent the formation of dental cavities. For the use of the floss there are different kinds of devices, in which the floss holders are placed at a distance from each other, and between which the dental floss is stretched. When using the present devices a problem is the gliding of the floss in the fastening grooves, which makes the cleaning troublesome, because the floss must be continuously adjusted. Another problem is that the loosening of the ultimate end of the floss may cause the floss to become loose from the fastening grooves and makes the use of the device more troublesome.

The aim of the invention is to bring forth a device for cleaning of the teeth, in which it is possible to fasten the dental floss firmly to the floss holders. Additionally, the aim of the invention is to bring about a device, which is simple to its construction, uncomplicated to produce, easy to use, hygienic and conserves of the dental floss.

SUMMARY OF THE INVENTION

On the device according to the invention have into the fastening grooves been formed ridges to prevent the floss from gliding in the fastening grooves. Also in the middle of the head on one of the floss holders on the upper edge of the fastening groove have been formed elevations for preventing the loosening of the ultimate end of the floss. The shape and the number of the ridges may vary in different applications, but they are arranged to prevent the dental floss from moving in the direction of the fastening groove. The dental floss is held on its spot and does not move during the cleaning of the teeth. After cleaning the dental floss is removed by pulling it away from the fastening groove, then it may be loosened easily. Also the ultimate end of the floss cannot get loose from its fastening without special measures to be taken.

In one preferred embodiment of the invention the ridges are formed in such a way, that they prevent the gliding of the dental floss in one direction only. In such a device the dental floss is always fastened in the same manner on the device.

In other preferred embodiment of the invention has a support, which has been placed between the floss holders so that the other end of the support is fastened to one floss holder near the fastening groove of the floss and the other end of the support is fastened to the shaft between the floss holders. When using the device the floss holders are put into the mouth so that the floss is between two teeth. The floss is pressed into the crack between the teeth. Then the teeth meet the support and they slide on the support. So the floss is brought slowly into the crack and not as quickly as usually.

BRIEF DESCRIPTION OF THE DRAWINGS

In the following the invention is explicated more in detail by referring to the attached drawings, out of which FIG. 1 presents one application of the device for cleaning of the teeth in accordance with the invention seen from the side, FIG. 2 illustrates another application of the device in accordance with the invention seen from the side and in cross-section.

Figure 3:
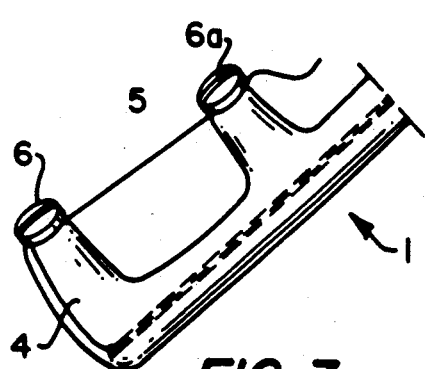
FIG. 3 illustrates the fastening of the dental floss on to the device in accordance with FIG. 2.
Figure 4:
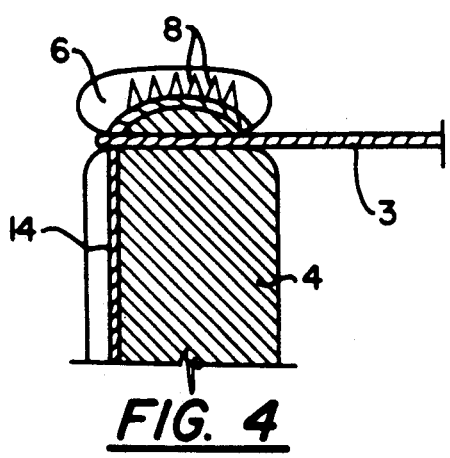
FIG. 4 illustrates the first floss holder head of the device in accordance with FIG. 3 in cross-section.

In the FIGS. 1 and 2 two embodiments of the device in accordance with the invention have been illustrated. The device in accordance with FIG. 1 is a so-called Y-shaped device and there the floss holders are an extension of the shaft. In the device in accordance with the FIG. 2 the floss holders are placed in such a manner, that they are stretching with regard to the shaft in a transverse direction away from the shaft. To both of the devices belong corresponding components. To the devices belong the shaft 1, inside which is formed the space 2 (not illustrated in FIG. 1). In the space 2 is placed the dental floss reel 3, which is placed on a holder 11 fastened in the lower part of the shaft. To the devices belong the floss holders 4, 5 in FIG. 2 and 4' and 5' in FIG. 1, fixed to the shaft. In the middle part of the shaft of the devices has been positioned the cutting element 10 for the cutting off of the dental floss.

As is illustrated FIG. 2 from the space 2 inside the shaft has been arranged a channel 12 to go through the shaft close to one of the floss holders 4. Between the floss outlet opening 13 and the head of the floss holder has been formed the guiding groove 14, which is arranged to guide and to hold the floss on its spot, whereat it does not glide on the side. In some applications the channel is arranged to go all the way to the immediate neighbourhood of the floss holder head, then the guiding groove is not needed at all.

In the FIGS. 3–7 the structure of the floss holder heads and the fastening of the floss have been presented. On the middle of the heads of the floss holders the fastening groove 6 or 6a has been formed, which divides the head in two mainly equally big parts. Between the head of the floss holders and the other part has been formed another fastening groove 6a, 7. The fastening grooves 6, 7 are to their form mainly wedgeshaped. Additionally, into the fastening grooves ridges 8 have been formed, which prevent the floss from gliding in the fastening groove in its length direction. In the illustrated embodiment the ridges are triangular in cross-section, but their shapes may vary.

Figure 5:
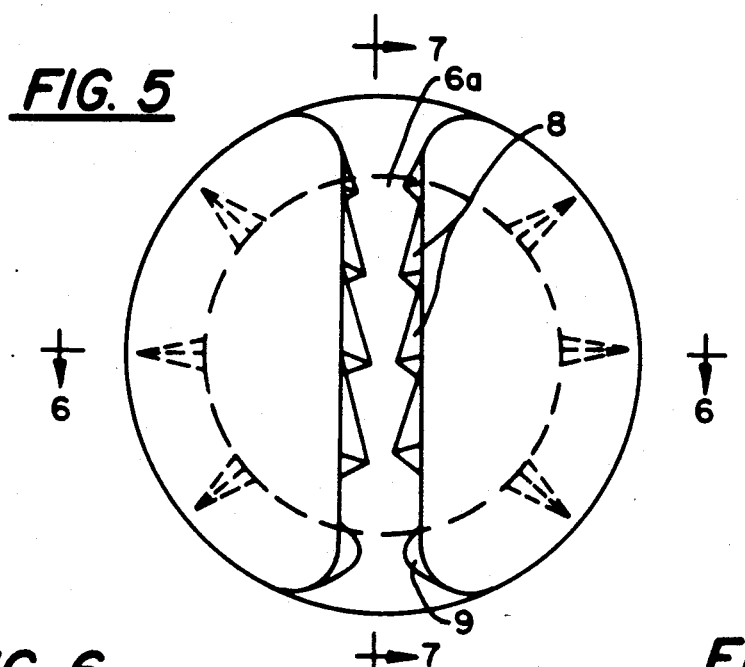
FIG. 5 illustrates the latter floss holder head of the device in accordance with FIG. 3 seen from the above.
Figure 6:
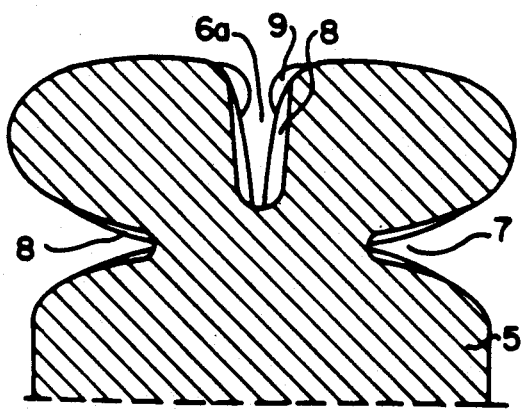
FIG. 6 shows the section 6—6 of FIG. 5.
Figure 7:
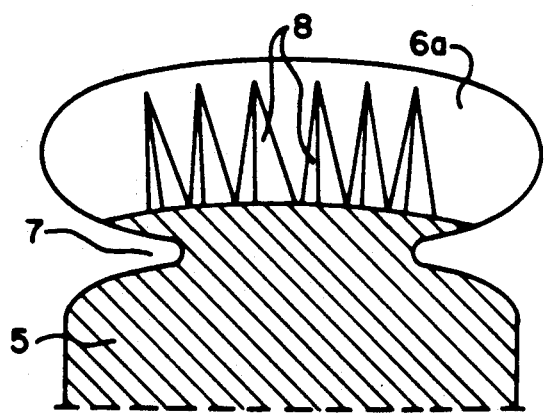
FIG. 7 shows the section 7—7 of FIG. 5.

In the FIGS. 5–7 the structure of the floss 5 is illustrated, to which the ultimate end of the dental floss is fastened. Onto the upper edge of the fastening groove 6a are formed the elevations 9, which prevent the loosening of the ultimate end of the floss. The structure of the other floss holder 4 is essentially similar, but it lacks the elevations.

When the device is not in use, the end of the dental floss is wound around the head of the floss holder 4. When the device is used the end of the floss is loosened from the holder and the floss is pulled away from the shaft. After this the floss is fastened by winding it around the both heads of the floss holders into the fastening grooves 6, 6a, 7. The floss can in case of need be pulled more than once between the floss holders, whereat the thickness of the floss can be adjusted effectively. The floss is, however, due to the form of the fastening grooves and the ridges, held firmly on its spot, when the device is used. As it is presented on the FIGS. 3 and 4 the floss is firstly put into the fastening groove 6 in the middle and thereafter into the fastening groove 7 on the side, whereat the floss on the side tightens the floss between the floss holders. After use the floss is loosened and cut off with the cutting element 10, which is positioned in the middle part of the shaft. The cutting element is not close to the heads of the floss holders, so it does not damage the corners of the mouth, when the device is used.

The device also has a curveshaped support 15. The support is placed between the floss holders 4, 5. The one end of the support is fastened to one floss holder 5 near to the fastening groove 7. The other end of the support is fastened to the shaft between the floss holders.

I claim:

1. A device for cleaning teeth with dental floss, comprising:

a shaft having a hollow portion formed therein for the containment of an amount of dental floss;

first and second spaced floss holders projecting from said shaft, said floss holders each having a wedge shaped fastening groove formed around a perimeter surface so as to define a head portion of said floss holder and to allow dental floss to be set therein;

said head portions also having a wedge shaped fastening groove formed on a top surface so as to allow dental floss to be set therein;

means for conducting dental floss from the hollow portion of said shaft to at least one of the fastening grooves of said first floss holder whereby in use said floss is set in both grooves in said first holder and extends therefrom to said second holder where it is set in both fastening grooves in said second holder; and a plurality of ridges formed in said fastening grooves to prevent said dental floss from moving relative to said floss holders;

said fastening groove on said top surface of said head portion of said second floss holder having at least one elevation formed on an upper edge for securely holding a free end of said dental floss.

2. A device as described in claim 1, further comprising:

a cutting element, for cutting dental floss, attached to said shaft at a point remote from said floss holders.

3. A device as described in claim 1, further comprising:

a support having first and second ends, said first end being adjacent one of said floss holders at a portion near said head portion, and said second end being adjacent a portion of said shaft between said floss holders.

4. A device according to claim 3, wherein said support has a continuously curved shape.

* * * * *

UNITED STATES PATENT AND TRADEMARK OFFICE
CERTIFICATE OF CORRECTION

PATENT NO. : 5,029.593
DATED : July 9, 1991
INVENTOR(S) : Huttunen

It is certified that error appears in the above-indentified patent and that said Letters Patent is hereby corrected as shown below:

On the title page: Item [63] Continuation insert--In-Part of PCT/F188/00084 filed May 31, 1988 abandoned--.

Signed and Sealed this

Ninth Day of January, 1996

Attest:

BRUCE LEHMAN

Attesting Officer

Commissioner of Patents and Trademarks